United States Patent [19]

Coggins et al.

[11] Patent Number: 4,683,137
[45] Date of Patent: Jul. 28, 1987

[54] TEMPERATURE SENSITIVE REASSORTANT VIRUSES AND A VACCINE AGAINST EQUINE INFLUENZA

[75] Inventors: Leroy Coggins, Cary, N.C.; Brian R. Murphy, Glen Echo, Md.; Dorothy F. Holmes, Groton, N.Y.; Lynne J. Anguish; James H. Gillespie, both of Ithaca, N.Y.

[73] Assignee: Cornell Research Foundation, Inc., Ithaca, N.Y.

[21] Appl. No.: 634,510

[22] Filed: Jul. 26, 1984

Related U.S. Application Data

[63] Continuation of Ser. No. 369,319, Apr. 16, 1982, abandoned.

[51] Int. Cl.$^4$ .................... A61K 23/00; A61K 39/12; A61K 39/145; C12N 7/00
[52] U.S. Cl. .................................... 424/89; 435/236; 435/235; 435/239
[58] Field of Search ................. 424/89; 435/236, 239, 435/235

[56] References Cited

U.S. PATENT DOCUMENTS

| | | | |
|---|---|---|---|
| 3,518,347 | 6/1970 | Pavilanis et al. | 424/89 |
| 3,869,546 | 3/1975 | Lund | 424/89 |
| 3,920,811 | 11/1975 | Lund | 424/89 |
| 3,992,522 | 11/1976 | Chanock et al. | 424/89 |
| 4,009,258 | 2/1977 | Kilbourne | 424/89 |
| 4,024,235 | 5/1977 | Weetall et al. | 424/89 |
| 4,206,287 | 6/1980 | Hannoun et al. | 424/89 |
| 4,318,903 | 3/1982 | Lobmann et al. | 424/89 |
| 4,442,205 | 4/1984 | Hamer et al. | 424/89 |
| 4,493,825 | 1/1985 | Platt et al. | 424/89 |
| 4,500,513 | 2/1985 | Brown et al. | 424/89 |

FOREIGN PATENT DOCUMENTS

113665 7/1984 European Pat. Off. .

OTHER PUBLICATIONS

Alexander, J. Roy. Soc. Med., vol. 75, pp. 799–811 (1982).
Masurel et al, Bull. Wld. Hlth. Org., vol. 34, pp. 885–893 (1966).
Kasel et al., Bull. Wld. Hlth. Org., vol. 41, pp. 447–452 (1969).
Romvory et al, Acta. Vet. Acad. Scien. Hung., vol. 24, pp. 457–461 (1974).
Rouse et al, Chemical Abstracts, vol. 72 (1970), abstract 72:98582a.
Rouse et al, Chemical Abstracts, vol. 72 (1970), abstract 72:98583b.
Pressler, Chemical Abstracts, vol. 72 (1970), abstract 72:136378y.
Frerichs et al, Chemical Abstracts, vol. 79 (1973), abstract 79:113745w.
Chemical Abstracts, CA, 77:32241K.
Chemical Abstracts, CA, 78:12247g.
Chemical Abstracts, CA, 94:116258K.
Chemical Abstracts, CA, 76:136983z.
Podchernyaeva et al, Biological Abstracts, 62:36966 (1976).
Chemical Abstracts, CA, 89:195230t.
Chemical Abstracts, CA, 79:113161c.
Chemical Abstracts, CA, 72:118773u.
Chemical Abstracts, CA, 80:92966x.
Chemical Abstracts, CA, 66:36141y.
Scholtissek et al, Virology, 118:28–34 (1982).
Brundage-Anguish et al, Am. J. Vet. Res., 43:869–894.
Kilborne, Science, 160:74–75 (1968).
Scholtissek et al, Virology, 65:325–328 (1980).
Scholtissek et al, Virology, 81:74–80 (1977).
Sherman et al, Ca–n. Vet. Jour., 18:154–158 (1977).
Sherman et al., J. Clin. Microbiol., 5:285–289 (1977).
Tolpin et al, Virology, 112:505–517 (1981).
Murphy et al, New Engl. J. Med., 286:1329–1332 (1972).
Fedson et al, J. Immunology, 107:730–737 (1971).
Van Wyke et al, J. Virol., 35:24–30 (1980).
Appleyard et al, J. Gen. Virol., 25:351–357 (1974).
Klenk, Virology, 68:426–439 (1975).
Murphy et al, Virology, 66:533–541 (1975).
Massicot et al, Virology, 101:242–249 (1980).
Tobita et al, Med. Microbiol. Immunol., 162:9–14 (1975).
Nath et al, Am. J. Vet. Res., 38:1059–1061 (1977).
Bulletin World Health Org., 58:585–591 (1980).
Spring et al, Virology, 66:533–532 (1975).
Murphy et al, Infect. and Immunity, 20:671–677 (1978).
Mills et al, J. Infect. Dis., 123:145–157 (1971).
Richman et al, J. Infect. Dis., 134:585–594 (1976).
Chanock et al, Viral Immunology and Immunopathology, 1975, Acadenuc Press, N.Y., pp. 291–316.
Murphy et al, Virology, 88:244–251 (1978).
Murphy et al, Infect. and Immunity, 20:665–670 (1978).
Jennings et al, Fed. Proc., 37:2072–2073 (1978).
Chanock et al, Rev. Infect. Dis., 2:421–431 (1980).
Murphy et al, Infect. Dis., 130:144–149 (1974).
Spring et al, Virology, 66:572–550 (1975).
Kemen, Proc. Am. Assoc. Equine Practitioners, 20:119–126 (1974).
Kemen, Hoofbeats, Jan. 1976, pp. 62–63.

Primary Examiner—Ronald W. Griffin
Attorney, Agent, or Firm—Jones, Tullar & Cooper

[57] ABSTRACT

This invention relates to a method and resulting temperature-sensitive (ts) reassortant virus produced by modifying wild-type equine influenza viruses by utilizing mutagenized human influenza viruses possessing ts lesions and shut off temperatures in the area of 37°–39° C., preferably 37°–38° C. When utilized as a vaccine for equines, these temperature-sensitive recombinant viruses have the facility to develop only mild symptoms while producing protection against infectious equine influenzal disease.

9 Claims, No Drawings

TEMPERATURE SENSITIVE REASSORTANT VIRUSES AND A VACCINE AGAINST EQUINE INFLUENZA

This is a continuation of application Ser. No. 369,319, filed Apr. 16, 1982, now abandoned.

BACKGROUND OF THE INVENTION

U.S. Pat. No. 3,992,522 teaches temperature-sensitive reassortant mutant viruses, method for their production and vaccines derived therefrom. One could not predict from this art, however, that a reassortant virus formed from a human influenza virus and an equine influenza virus would provide a reassortant virus which could be used to provide a vaccine which on the one hand would not cause serious disease in an equine, yet on the other hand would induce effective resistance in an equine to equine influenzal disease produced by challenge with a virulent wild-type equine influenza virus. Temperature-sensitive (ts) mutation affords the possibility of site-specific attenuation for the lower respiratory tract. The acquisition of temperature-mutant defects in a strain of influenza virus has been shown in mice to be associated with diminished virulence, though the antibody producing stimulus remained (British Medical Journal, 1969, 3:757–758). Replication of mutants with markedly restricted growth at 37° C.–38° C. appears to be greatly limited in the lower respiratory tract, the major site of significant pathology, which has a temperature of 37° C. in humans. However, the mutants should grow with reasonable efficiency in the cooler passages of the upper respiratory tract, which have a temperature of 32°–34° C. In this manner, ts mutants grow primarily in the upper respiratory tract and stimulate immunologic defense mechanisms without producing symptoms in the lower tract. Additionally, ts mutants are often partially defective at permissive temperatures (32°–34° C.), and this property offers the possibility of attenuation for the upper respiratory tract as well.

Much of the prior art relative to the present invention is of the literature variety, e.g.:

Murphy et al, "Temperature-Sensitive Mutants of Influenza Virus II Attenuation of ts Recombinants for Man", *The Journal of Infectious Diseases*, Vol. 126, No. 2, August 1972, pages 170–178.

Murphy et al, "Temperature Sensitive Mutants of Influenza Virus III Further Characterization of the ts-1[E] Influenza A Recombinant (H3N2) Virus in Man", *J. of Infectious Diseases*, 128:478–487, 1973.

Beare et al, "Recombinant Influenza-A Viruses as Live Vaccines for Man", *Lancet*, 2:1271–1273, 1971. This Beare journal article does refer, as the title indicates, to a recombinant influenza-A virus as live vaccines for man; however, at page 1272, Table 2, it shows that there is no correlation between restricted growth at 39° and attenuation. This is brought out by the notation that the virulent parent virus (939) is restricted to 39° and the attenuated virus (PR8) replicates well at 39°. Additionally, clone 7 grows well at high temperature and is virulent, whereas clone 64C similarly grows well at 39° but is attenuated. Beare demonstrates simply that the mating of an avirulent virus (PR8) and a virulent virus (939) can give rise to clones of viruses with a spectrum of virulence for man. However, in this article there is no specific characteristic; i.e., temperature sensitivity, associated with this attenuation. The Beare article also utilizes an avirulent virus produced by serial passage in animal and tisue culture rather than by chemical mutagenesis.

Maassab et al, "Hybrid Formation of Influenza Virus at 25° C.", *Fed. Proc.*, 30:413, 1971 [abstract]. This immunology abstract and the parent article, *Proc. Soc. Exp. Biol. and Med.*, 139:768, March 1972, relate to the procedure of Dr. Maassab to produce attenuated viruses of influenza A virus, which is similar to but distinct from the present procedure. Maassab produces an attenuated parent virus by growth of virus at low temperature, a well-known technique for the production of live attenuated virus vaccine strains. Live measles vaccine have been produced in thiss manner. The present chemical technique involves the chemical mutagenesis of influenza A virus and the subsequent isolation of viruses that are temperature sensitive. The end result is to produce viruses that grow at 34° but not at 39°, and these are the ts attenuated viruses. The Maassab technique, which involves a transfer of a defect from an attenuated strain to a new wild-type virus by genetic recombination, is similar to the present invention, but the method of production of attenuated viruses is different.

MacKenzie, "Virulence of Temperature-Sensitive Mutants of Influenza Virus", *Br. Med. J.*, 3:757–758, 1969. With reference to this MacKenzie article, it is noted that distinct from the present development, MacKenzie did not work with recombinant ts viruses, although he did demonstrate the ts mutants of influenza A viruses produced by chemical mutagenesis were attenuated for animals. More important, the virus preparations in the journal article were not suitable for human use and no attempt was made to pass these ts defects to different influenza A viruses by recombination.

Recent epidemiological studies (Ingram et al, *Equine Infectious Diseases IV* (Proc. of the 4th Internat. Conf. Equine Infec. Dis.) Barnes et al eds. Vet Pub. Inc. Princeton, N.J. (1978) p.p. 329–338. Kemen, *Proc. Am. Assoc. Equine Practitioners*, 20:119–126, 1974; and Kemen, *Hoofbeats*, January 1976, pp. 62–63), undertaken in areas of high equine density such as racetracks, training areas, shows and breeding farms have shown that the most important agent causing clinical respiratory disease in the horse is the equine influenza virus. Presently available inactivated equine influenza vaccines have several limitations. First, because of occasional deleterious side-effects in vaccinated horses and incomplete protection, many horsemen are abstaining from a regular vaccination program for their animals. Second, these vaccines provide only a short-lived program which lasts only 3–4 months under intense challenge and requires several vaccinations each year to provide adequate protection (Ingram et al, supra; Burrows, *Amer. Assoc. Equine Pract.*, 1979, p. 37–48).

Unlike the human influenza viruses, there has not been significant antigenic drift in the two equine influenza viruses (Burrows, supra). In addition, infection of horses with the wild-type virus provides a high degree of protection as indicated by the high frequency of disease in two- and three-year-olds with little clinical evidence of reinfection in previously exposed older horses (Ingram et al, supra; Kemen, supra). These factors support the idea that the development of an effective live virus vaccine for equine influenza would be valuable in the control of this disease since a live vaccine might stimulate immunity like that of natural infection.

In recent years, conditional-lethal, temperature-sensitive mutants of human influenza A viruses have been produced characterized and evaluated as candidate live virus influenza vaccines in humans with some promising results (Chanock and Murphy, *Rev. Infect. Dis.*, 2:421-432, 1980). The use of ts mutants as vaccines offers several advantages. The location of the ts lesion on the viral genome can be determined and the level of in vitro temperature sensitivity of plaque formation measured in the laboratory (Murphy et al, *J. Infect. Dis.*, 130:144-149, 1974; Spring et al, *Virology*, 66:542-550, 1975; and Murphy et al, *Infect. Immun.*, 20:665-670, 1978).

Attenuated ts vaccine viruses can be evaluated for genetic stability during production, experimental trials, and later usage in the field with the ts lesion serving as a marker for vaccine virus.

Ts reassortant clones which are restricted in replication in vitro at 37°-38° C. multiply efficiently in the upper respiratory tract of man and hamsters and induce local and systemic immune responses which protect against wild-type influenza virus (Murphy et al, *Infect. Dis.* 126:170-178, 1972; Murphy et al, *J. Infect. Dis.*, 128:479-487, 1973; Murphy et al, *Virology*, 88:244-251, 1978; Jennings et al, *Fed. Proc.*, 37:2072-2073, 1978; Mills et al, *J. Infect. Dis.*, 123:145-157, 1971; and Richman et al, *J. Infect. Dis.*, 134:585-594, 1976). However, because the replication of the virus is sensitive to temperature, these viruses replicate inefficiently in the warmer, lower respiratory tract (approximately 38° C. in the horse) and, therefore, should not produce the cough characteristic of the wild-type equine influenza virus infection. It is hoped that the increased stimulation of local and systemic immune systems by viral replication could decrease the need for frequent vaccinations, with perhaps annual vaccination in horses being sufficient (Chanock et al, *Viral Immunology and Immunopathology*, 1975, Academic Press, NY., P 291-316).

DESCRIPTION OF THE INVENTION

This invention relates to a method and resulting temperature-sensitive (ts) reassortant virus produced by modifying wild-type equine influenza viruses by utilizing mutagenized human influenza viruses possessing ts lesions and shut off temperatures in the area of 37°-39° C., preferably 37°-38° C. When utilized as a vaccine for equines, these temperature-sensitive recombinant viruses have the facility to develop only mild symptoms while producing protection against infectious equine influenzal disease.

In general, the present method and resulting product are directed to a method for producing a temperature-sensitive hybrid human/equine influenza-type virus which comprises mating a chemically mutagenized temperature-sensitive human influenza virus having at least one and preferably at least two ts lesions, with a virulent wild-type equine influenza virus to produce a new reassortant (sometime called recombinant) virus with equine antigenic components. The new reassortant viruses of the invention have at least two but no more than six of its eight genes derived from the human ts mutant with the remaining genes being derived from the wild-type equine virus.

As to the temperature-sensitive human influenza virus which can be employed to form the reassortant viruses of the invention, virtually any chemically mutagenized conditional-lethal temperature-sensitive (ts) mutants containing at least one and preferably at least two (ts) mutants can be employed. U.S. Pat. No. 3,992,522, hereby incorporated by reference in its entirety, describes the preparation of various of such ts mutants from human influenza A type viruses including:

Influenza A/1965-ts-1 (H2N2)
Influenza A/Hong Kong/1968-ts-1[A] (H3N2)
Influenza A Double recombinant 10B (H0N2)
Influenza A/Hong Kong/1968-ts-1[E] (H3N2)

as well as further recombinant viruses such as one denoted ts-1[E] which was produced from wild-type influenza A/Hong Kong/1968 (H3N2) and the 1965-ts-1 mutant noted above.

As to the wild-type equine influenza virus employed to form the reassortant viruses of the invention any virulent equine influenza virus of either the $A_1$ or $A_2$ sub-groups may be employed.

The generalized method of production of temperature-sensitive recombinants involves a mixed infection of cells grown in tissue culture incubated at a permissive temperature (34° C.) using two viruses: (1) a temperature-sensitive virus of one serotype, and (2) another serotype non-ts virus that one desires to attenuate. Antiserum to the ts virus must be available that will neutralize the ts parent virus but have no effect on the non-ts virus. The cells are infected simultaneously at a multiplicity of infection of 1 for each parent virus. The progency of this mating is then plaqued on monolayer cultures at the permissive temperature in the presence of antisera to the ts parent virus. The virus present in the plaques is then inoculated into tissue culture, incubated at the permissive temperature, and harvested. The virus present in this harvest is then characterized for its serotype and temperature sensitivity. The virus which has both the serotype of the non-ts parent and the ts defect of the ts parent is considered to be the desired recombinant. The desired recombinant ts virus is then subjected to two successive plaque-to-plaque passages.

After the last plaque passage, the virus is then grown up in tissue culture and the serotype and ts characteristic again determined. This method of plaque-to-plaque purification insures that the recombinant virus is both genetically homogeneous and stable. The ts recombinant virus is ready at this point to be used as a seed for production of larger quantities of virus.

EXAMPLE

Temperature-sensitive (ts) reassortants of an equine influenza, subtype A-1, were produced by mating a human influenza ts donor virus with an equine influenza A/Cornell/16/74 wild-type (wt) virus and by isolating a ts reassortant virus possessing the equine hemagglutinin and neuraminidase surface antigens. Two equine ts reassortant clones, 8B1 and 71A1, were produced which had an in vitro shutoff temperature for plaque formation of 38° and 37° C., respectively. The human ts donor virus had ts mutation(s) on the polymerase 3 (P3) and nucleoprotein (NP) genes so that a ts equine reassortant virus could have either or both of these ts genes. It was found by complementation analysis that reassortant clone 8B1 had a ts lesion on the P3 gene and clone 71A1 had ts lesions on the NP and P3 genes. An analysis of the parental origin of the genes in each ts equine reassortant virus indicated that clone 8B1 received 6 of its 8 genes and clone 71A1 three of its eight from the equine parent virus, the remainder genes being from the human ts donor virus. The growth of both clones was restricted in the lungs of hamsters, but similar to that of the equine wild-type virus in the nasal turbinates. Each virus isolate obtained from the hamster's lungs or nasal turbinates retained the ts phenotype. These findings form the basis for further evaluation of the equine ts reassortant viruses for their level of attenuation and immunogenicity in horses.

MATERIALS AND METHODS

Viruses

The wild-type equine influenza virus, subtype A-1, A/Cornell/16/74 (Heq1 Neq1 [H7N7 by new WHO nomenclature (Bulletin of World Health Organization 58:585–591 (1980)] was originally isolated in 1973 from an outbreak of equine influenza in Florida. It was subsequently passaged intranasally through 4 Shetland-type ponies to check for virulence, then grown in Madin-Darby Canine Kidney Cells (MDCK), plaque purified twice by passage at 34° C. and 39° C., and then grown twice in MDCK culture (TCID $10^{6.5}$/ml). This virus was designated A/Cornell/74 cone 2A. Before being used in the production of a temperature-sensitive reassortant equine influenza, clone 2A was shown to produce a fever, hyperemia and congestion of the nasal mucosa, and a serous nasal discharge in experimental ponies. Wild-type human A/Udorn/307/72 (clone 3A1) (H3N2), which had been passaged 6 times in primary calf kidney cells BK, once in eggs and one in MDCK cells, was used as a control virus in the hamster studies and tissue culture assays.

The production of the human influenza A ts mutant used as a donor of its ts genes to the A/Cornell/74 equine virus has not been described previously. This ts virus contains ts mutations on the genes coding for the P3 polymerase protein and the nucleoprotein (NP) gene and was produced by mating the A/Victoria/75-ts-1A2 (clone 65A1) $H3_{75}N2_{65\ or\ 68}$ virus (ts P3 gene) (Murphy, B. R., Markoff, L. J., unpublished observation) with the A/Udorn/307/72-ts-368 $H3_{72}N2_{72}$ virus (ts NP gene). This latter ts virus was produced by chemical mutagenesis by Dr. Lewis Markoff at the Laboratory of Infectious Diseases, National Institutes of Health, Bethesda, Md. and was shown by complementation and segregational analysis to contain a ts NP gene (Dr. Markoff, unpublished observation). A reassortant virus from the above mating, designated A/Udorn/72-ts-20A1 ($H3_{72}N2_{72}$), was shown by genetic analysis to contain the ts P3 gene from the A/Victoria/75-ts-1A2 parent and the ts NP gene from the A/Udorn/72 ts 368 virus using methods previously described (Murphy et al, *Infect. Immun.*, 20:665-670, 1978; Spring et al, *Virology*, 66:522-532 (1975); Murphy et al, *Infect. Immun.*, 20:671-677, 1978; Massicot et al, *Virology*, 101:242-249, 1980). The A/Udorn/72-ts-20A1 reassortant was passaged five times in BK including a plaque-to-plaque passage (titer $10^{6.5}$ $TCID_{50}$/ml) and had a shutoff temperature for plaque formation of 37° C. The two ts parents of clone 20A1, A/Udorn/72 (clone 368A2) and A/Victoria/75-ts-1A2 (clone 65A1), were used in complementation studies as "probe" viruses. Clone 368A2 had been passaged four times in Bk and twice in eggs. It contained a ts lesion on the NP gene (complementation group 2). Clone 65A1 had been passaged 5 times in BK and once in eggs and had a ts lesion on the P3 gene (complementation group 2) (Spring et al, *Virology*, 66:522-532, 1975; Mills et al, *J. Infect. Dis.*, 123:145-157, 1971).

Tissue Culture and Infectivity Assays

Infectivity and plaque assays have been described previously (Murphy et al, *Infect. Immun.*, 20:665-670, 1978) except that 12-well plastic tissue culture plates were used for plaque tests instead of 6-well plates. The MDCK cell monolayers used throughout this study (Tobita, et al., *Med. Microbiol. Immunol.*, 162:9-14 (1975); Nath et al, *Am. J. Vet. Res.*, 38:1059-1061, 1977) were prepared by Flow Laboratories. Media consisted of either Eagles minimal essential medium with Earle's salts or 50% Eagles #2 and 50% Medium 199 (M A Bioproducts) containing 0.29 mg L-glutamine, 2.5 μg amphotericin B and 66-μg gentamycin per ml. For cell growth, 10% fetal bovine serum (screened for suitability for replication of influenza virus) was included; for virus growth medium, serum was deleted and trypsin was added at a final concentration of 1 μg/ml. In the hamster infectivity studies, transport medium consisting of 50% Eagles #2 and 50% Medium 199 and containing 0.5% gelatin and twice the concentration of antibiotics was used to collect the virus from tissues. Plaque overlay consisted of L-15 medium with L-glutamine, trypsin, and antibiotics at the above concentrations plus 0.8% agarose. The addition of trypsin to virus growth medium enhanced the formation of visible plaques which made addition of erythrocytes to visualize titration endpoints unnecessary in most cases (Appelyard et al, *J. Gen. Virol.*, 25:351-357, 1974; Tobita, et al., *Med. Microbiol. Immunol.*, 162:9-14, 1975; Klenk et al, *Virology*, 101:242-249, 1980).

Production of Equine Reassortants

The procedures for the production of reassortants were similar to those previously described (Murphy et al, *Virology*, 66:533-541, 1975; Spring et al, *Virol.*, 66:522-532, 1975). Briefly, A/Udorn/72 ts-20A1 and A/Cornell/74 clone 2A were mixed at an M01 of 1 for each virus and then added to washed monolayers in 6-well plastic tissue culture plates. After a 1 hour adsorption at room temperature, the cells were washed 5 times, overlayed with plaquing medium and incubated for 24 hours at 34° C. The progeny viruses were harvested, serially diluted (10-fold) and incubated for 1 hour at room temperature with an equal volume of a 1:200 dilution of hyperimmune ferret antiserum against A/England/42/72 (H3N2) virus. This concentration of antiserum had previously been shown to reduce the titer of the A/Udorn/72-ts-20A1 virus by at least 100-fold but did not neutralize the equine parent virus. The mixtures were then inoculated onto mono-layers in 6-well plates and observed for plaque formation. A/Cornell/74-ts reassortant viruses were selected from the reassortant progeny and cloned as previously described (Richman et al, *Virology* 66:551-562, 1975). The virus clones were plaque purified 3 times.

Characterization of Equine ts Reassortants

The procedure for determining the efficiency of plaque formation of selected virus clones at 34, 36, 37, 38 and 39° C., has been described (Murphy et al, *Infect. Immun.*, 20:665-670, 1978; Murphy et al, *Infect. Immun.*, 20:671-677, 1978), except that 12-well plates were used in the present study.

Plate complementation tests, using A/Victoria/75-ts-65A1 and A/Udorn/75-ts-368A2 viruses as ts probes, were performed as previously described (Murphy et al, *Infect. Immun.*, 20:665-670, 1978; Spring et al, supra;

Murphy et al, *Infect. Immun.*, 20:671–677, 1978), except that the viruses were not first incubated at 4° C.

The hemagglutinin present on each ts reassortant was characterized by standard microtiter hemagglutination inhibition (HI) tests using monospecific goat anti-H equi-1 and ferret anti-H3 antisera. The neuraminidase pesent on the reassortant was characterized using neuraminidase inhibition (NI) tests and goat anti-N equi-1 antiserum as previously described (Murphy et al, *New Engl. J. Med.*, 286:1329–1332, 1972; Fedson et al., *J. Immunol.*, 107:730–737, 1971).

Polyacrylamide Gel Electrophoresis (PAGE) of Equine ts Recombinant Virion RNA To determine the parental origin of individual genes in the equine ts reassortant clones 71A1 and 8B1, virion RNA (v RNA) from these two viruses was analyzed as previously described (Massicot et al, *Virology*, and stored at $-70°$ C. until titrated. Virus was titrated in 24-well disposable tissue culture plates at 34° C. and the endpoint after 4 days of incubation was expressed as $TCID_{50}/gm$ of tissue. The supernatants from the wells inoculated with the two lowest dilutions which showed viral CPE were harvested and tested for efficiency of plaque formation at 34° and 39° C. to determine if there was loss of the ts phenotype after replication in vivo.

Selection and Characterization of Cornell/74-ts Reassortant Viruses

The reassortant progeny from the double infection of the human ts and equine wild-type viruses were characterized. the neuraminidase and hemagglutinin subtype, efficiency of plaque formation (EOP), shutoff temperature for growth and complementation group(s) of the parent strains and selected ts equine reassortant clones are shown in Table 1.

TABLE 1

| Influenza A Virus | Hemagglutinin Subtype | Neuraminidase Subtype | Characteristics of Parent Strains and A/Cornell/74-ts Recombinants Log-10 Reduction in Virus Titer (PFU/0.1 ml)* | | | | Shut-off Temperature | Complementation Group of ts Lesion(s) |
|---|---|---|---|---|---|---|---|---|
| | | | 36° | 37° | 38° | 39° | | |
| A/Cornell/74 wild type | H-equi-1 | N-equi-1 | 0.1 | 0.1 | 0.1 | 0.1 | >39 | NA |
| A/Udorn/72 ts clone 20A1 | $H3_{72}$ | $N2_{72}$ | 1.0 | >3.4 | >4.9 | >4.9 | 37 | 1,2 |
| A/Cornell/74 ts recombinant clones | | | | | | | | |
| 8B1 | H-equi-1 | N-equi-1 | 0.3 | 0.6 | >5.7 | >5.7 | 38 | 1 |
| 71A1 | H-equi-1 | N-equi-1 | 0.9 | >3.2 | >5.4 | >5.4 | 37 | 1,2 |

*Average of 2-5 tests. Reduction at indicated temperature (°C.) from titer at permissive temperature.
+Defined as the lowest temperature which gives 2 Log-10 reduction in titer.
≠Complementation-recombination group 1 ts lesion is on the P3 gene, group 2 is on the NP gene.
NA = Not applicable 101:242–249, 1980). The migration patterns of v RNA obtained from reassortant viruses were compared to that of the A/Udorn/72-ts-20A1 and Cornell 74 wild-type clone 2A parent viruses.

The conditions used to see differences in the migration rates of the parental RNAs were as follows: genes, 2,3,4 and 8 on a 20 cm gel of 2.8% acrylamide and 6M urea for 17.5 hours at 28.5° C. and 95 volts; gene 1 on a 20 cm gel of 3.0% acrylamide and 6M urea for 19 hours at 29° C. and 100 volts; and genes 5 and 7 on a 20 cm gel of 2.6% acrylamide run in 6M urea for 16 hours at 26° C. and 110 volts. Gene 6 (nucleoprotein) was kindly identified by Kathleen Van Wyke at St. Jude's Hospital using monoclonal antibodies in an enzyme-linked immunosorbent assay as previously described (Van Wyke et al, *J. Virol.* 35:24–30, 1980).

Hamster Studies

After intraperitoneal pantobarbitol anesthesia, groups of six-week-old female Golden Syrian hamsters (Lakeview Animal Farms, Newfield, N.J.), were innoculated intranasally with 0.1 ml of virus suspension that contained $10^{5.5}$ $TCID_{50}$. Five to 8 animals were sacrificed daily for 4 days (clones 2A, 8B1, 71A1 and 20A1) or 2 days (clone 3A1) and lungs and nasal turbinates were removed aseptically. The lungs were ground in 7 ml of transport medium in a Ten-Broeck type tissue grinder (10% w/v); turbinates were ground with an apothecary mortar and pestle with 0.5 ml of transport medium and roughly 3 g of sterile sea sand, after which 5.0 ml of medium were added (5% w/v). All samples were then centrifuged and the supernatant divided into 3 aliquots of 77 viable plaques picked, two (2.6%) possessed the equine hemagglutinin and neuraminidase and the ts phenotype (designated clones 8B1 and 71A1). Plaques were not produced at 39° C. when clone 71A1 was grown in mixed culture with either ts virus probe in the complementation assay and this indicated that clone 71A1 had received both the ts NP and ts P3 gene from its A/Udorn/72-ts 20A1 parent. In addition, the clone 20A1 ts parent and its clone 71A1 equine ts progeny exhibited the same EOP (37° C. shutoff temperature). When clone 8B1 was cultured with the ts probes, plaques were observed at 39° C. in the 8B1×368A2 (NP lesion) mixed cultures but not in the 8B1×65A1 (P3 lesion) cultures. Thus, clone 8B1 possesses a ts lesion on the P3 but not on the NP gene and has a shutoff temperature of 38° C. An A/Cornell/74-ts reassortant that possessed only a ts NP gene was not isolated.

The parental origin of the genes in A/Cornell/74-ts clones 8B1 and 71A1 was determined by a comparison of the relative migration of RNA of parental and reassortant viruses in PAGE, Table 2. (These assignments of parenteral origin are based on antigenic analysis and on the order of migration of the v RNA segments from the human virus whose genetic map is known.) The order of migration of the P1-3 genes of the equine virus were different from the Udorn. In the Udorn/72 preparation RNA 1, 2 and 3 are genes P3, P1 and P2, respectively, but in the Cornell/74 wild-type 1 preparation, RNA 1 is P2. The two RNA segments which migrated just ahead of the equi P2 gene must be the P1 and P3 genes of the equi virus but which RNA segment corresponds to which gene has not been determined. Most of the genes of clone 71A1, including the ts, NP and P3 genes, migrated with the human Udorn/72-ts parent the equine ts reassortant viruses, like their human ts parent, did not lose the ts phenotype in the hamster.

TABLE 3

Infection of Hamsters with Wild Type and ts Viruses

| Influenza A Virus | Animals Infected on Indicated Day* | | | | Genetic Stability # Isolates ts+/# tested** | |
|---|---|---|---|---|---|---|
| | 1 | 2 | 3 | 4 | Lungs | Nasal Turbinates |
| A/Cornell/74 wild type clone 2A | 100 | 89 | 75 | 80 | NA | NA |
| A/Udorn/72 wild type clone 3A1 | 100 | 89 | ND | ND | NA | NA |
| A/Udorn/72 ts clone 20A1 | 89 | 75 | 63 | 25 | 0/2 | 0/19 |
| A/Cornell/74 ts recombinant clones | | | | | | |
| 8B1 | 100 | 100 | 75 | 43 | 0/12 | 0/25 |
| 71A1 | 63 | 63 | 38 | 14 | 0/2 | 0/14 |

*Infection defined as recovery of virus from the lungs and/or nasal turbinates.
**ts+ is defined as an isolate that produces plaques at the restrictive temperature (39° C.). All viral isolates from lung and nasal turbinates were tested.
NA = Not applicable.
ND = Not determined.

genes, indicating that they were derived from this parent. However, except for the P1 and ts P3 gene, all of clone 8B1's genes co-migrated with the Cornell/16/74 clone 2A parent virus genes, indicating that clone 8B1's genes were derived mainly from its equine parent.

TABLE 2

Genotype of Equine Influenza ts Reassortants

| Gene Coding For: | Clone 71A1 | Clone 8B1 |
|---|---|---|
| Polymerase 1 | Human | Human |
| Polymerase 2 | Human | Equine |
| Polymerase 3 | Human (ts) | Human (ts) |
| Hemagglutinin | Equine | Equine |
| Neuraminidase | Equine | Equine |
| Nucleoprotein | Human (ts) | Equine |
| Matrix proteins | Human | Equine |
| Nonstructural proteins | Equine | Equine |

Replication of Parent and ts Progeny Viruses in Hamsters

The replication of the A/Cornell/74-ts viruses was restricted in the lungs but not the nasal turbinates of hamsters. The $\log_{10}$ reduction in lung virus titer as compared to its wild-type virus was 5.7 for the human ts-20A1, 3.0 for ts-8B1 and 3.6 for ts-71A1. The frequency with which 8B1 was shed (Table 3) (% in animals) was similar to the wild-type 2A on all 4 days, starting with 100% of animals on day 1 and reducing to approximately 60% on day 4.

None of the hamsters which were infected with ts viruses shed ts+ (revertant) virus which indicates that One of the ts equine recombinants (8B1) was selected to begin immunogenicity and safety studies in horses. This virus was chosen because it grew to higher titer in the MDCK cell line and because it contained a higher % of genes derived from the equine parent and might, therefore, be expected to grow more readily in the horse. Ponies held in isolation units were screen for pre-existing antibody to Equine $A_1$ influenza virus, and were infected by aerosolization with 8B1 virus. Animals were observed daily for clinical signs. Temperatures were taken twice daily and naso-pharngeal swabs for virus isolation were obtained for 7 days post-infection. 8B1 was found to successfully infect ponies as evidenced by virus recovery from the naso-pharynx and the subsequent development of serum hemagglutination-inhibiting (HI) antibody in ponies. Clinical signs following infection with 8B1 were limited to slight nasal hyperemia and an occasional serous nasal discharge. None of the animals became febrile or developed a cough. Virus recovered from the nasal swabs was tested and determined to still retain its temperature-sensitive property.

Four weeks after 8B1 infection, ponies were challenged (also by aerosolization) with "wild type" equine influenza $A_1$ virus. The challenge virus has been previously shown to induce fever and nasal discharge in inoculated horses and can be recovered from naso-pharyngeal swabs for up to 5 days. With one exception, the 8B1-vaccinated ponies had no febrile response following challenge and challenge virus was not recovered from the naso-pharynx.

Fourteen ponies were vaccinated with 8B1 and all were challenged with "wild-type" virus. Six additional ponies served as challenged controls.

TABLE 4

Development of a Temperature-Sensitive Equine Influenza Vaccine - Summary of Initial Experimental Ponies

| Pony No. | Vaccine Doses | Pre-Inoculation Titers | Max. Post Vac. Titers | Max. Body Temp. post Vac. | Days to Maximum Titer | Post Vac. Virus Recovery (Days) | Max. Body Temp. Post-Challenge | Post Chall. Wild-type Virus Recov. | Maximum Post Chall. Titer (HI) | Days to Maximum Titer |
|---|---|---|---|---|---|---|---|---|---|---|
| 600 | 1 | Neg. | 40 | 100.7 | 22 | 2,3,4,5,6 | 100.5 | None | 40 | 5 |
| 601 | 1 | Neg. | 10 | 100.6 | 29 | 2,3 | 104.1 | Days 2, 3 | — | — |
| 603 | 3 | Neg. | 20 | 100.8 | 14 | None | 100.0 | None | 40 | 14 |
| 605 | 3 | Neg. | 20–40 | 100.6 | 27 | None | 100.6 | None | 80 | 14 |
| 606 | 2 | Neg. | 10 | 100.7 | 27 | None | 99.9 | None | 40 | 14 |
| 617 | 2 | Neg. | 40–80 | 100.8 | 27 | None | 100.7 | None | 40 | 14 |
| 616 | 1 | Neg. | 10 | 100.9 | 21 | 3 | 100.8 | Day 3 | 20–40 | 21 |
| 625 | 1 | Neg. | 20 | 100.0 | 15 | 3 | 100.8 | None | 20 | 14 |
| 624 | 1 | Neg. | 10 | 100.6 | 21 | 3 | 100.9 | None | 20–40 | 14 |

TABLE 4-continued

Development of a Temperature-Sensitive Equine Influenza Vaccine - Summary of Initial Experimental Ponies

| Pony No. | Vaccine Doses | Pre-Inoculation Titers | Max. Post Vac. Titers | Max. Body Temp. post Vac. | Days to Maximum Titer | Post Vac. Virus Recovery (Days) | Max. Body Temp. Post-Challenge | Post Chall. Wild-type Virus Recov. | Maximum Post Chall. Titer (HI) | Days to Maximum Titer |
| --- | --- | --- | --- | --- | --- | --- | --- | --- | --- | --- |
| 622 | 1 | Neg. | 10 | 100.7 | 15 | 3,5 | 101.4 | None | 40 | 21 |
| 483F$_6$ | 1 | Neg. | 40 | 100.5 | 12 | 2 | 100.4 | None | 1 | 1 |
| 619 | 1 | Neg. | 20 | 100.6 | 28 | 2,3,4 | 100.2 | None | 20 | 1 |
| 621 | 1 | Neg. | 20 | 100.6 | 28 | 2,3,4 | 100.4 | None | 80 | 12 |
| 623 | 1 | Neg. | ≦10 | 100.8 | 7 | None | 101.2 | None | 10 | 26 |
| Challenge Controls | | | | | | | | | | |
| 515F$_6$ | — | Neg. | — | — | — | — | 104.0 | Days 2,3,4,5 | ND | — |
| 611 | — | Neg. | — | — | — | — | 102.2 | Days 2,3,4,5 | 80 | 21 |
| 618 | — | Neg. | — | — | — | — | 102.4 | Days 2,3,5 | 20 | 14 |
| 620 | — | Neg. | — | — | — | — | 101.4 | Days 2,3,5 | 20 | 14 |
| 451F$_6$ | — | Neg. | — | — | — | — | 102.0 | Days 2,3,4,5,6 | 80 | 14 |

We claim:

1. A temperature-sensitive virus capable of providing an equine influenza vaccine which is a reassortant mutant virus, formed by mating a wild-type equine influenza virus of the A$_1$ or A$_2$ subgroups with chemically mutagenized and temperature-sensitive human influenza virus having a shut off temperature in the area of 37° C. to 39° C., said reassortant virus having at least one temperature-sensitive gene and at least two but no more than six human influenza virus derived genes, and being further characterized as having the serotype of the equine influenza virus and the temperature-sensitive defects of the human virus.

2. A virus as in claim 1 wherein the virus has six equine virus genes and two human virus genes.

3. A temperature-sensitive virus capable of providing an equine influenza vaccine which is a reassortant mutant virus, formed by mating a wild-type equine influenza virus of the A$_1$ or A$_2$ subgroups with chemically mutagenized and temperature-sensitive human influenza virus having a shut off temperature between 37° C. and 39° C., said reassortant virus having at least one temperature-sensitive gene and at least two but no more than six human influenza virus derived genes and being further characterized as having the serotype of the equine influenza virus and the temperature-sensitive defect of the human virus.

4. A vaccine against equine influenza comprising the virus of claim 1.

5. A vaccine against equine influenza comprising the virus of claim 2.

6. A vaccine against equine influenza comprising the virus of claim 3.

7. A method of protecting an equine against equine influenza which comprises inoculating said equine with a vaccine comprises the virus of claim 1.

8. A method of protecting an equine against equine influenza which comprises inoculating said equine with a vaccine comprises the virus of claim 2.

9. A method of protecting an equine against equine influence which comprises inoculating said equine with a vaccine comprising the virus of claim 3.

* * * * *